United States Patent [19]

DePalma et al.

[11] 4,175,233
[45] Nov. 20, 1979

[54] FLOW CELL AND METHOD FOR CONTINUOUSLY MONITORING DEPOSITS ON FLOW SURFACES

[75] Inventors: Vito A. DePalma, Tonawanda; Robert E. Baier, Buffalo, both of N.Y.

[73] Assignee: Calspan Corporation, Buffalo, N.Y.

[21] Appl. No.: 910,165

[22] Filed: May 26, 1978

[51] Int. Cl.² ............................................. G01N 21/26
[52] U.S. Cl. .................................... 250/343; 250/435; 356/432
[58] Field of Search ............... 250/343, 344, 345, 373, 250/428, 432, 435; 356/38, 51, 432, 436, 441; 73/53, 61.4; 23/230 R, 230 B, 253 R; 324/71 CP

[56] References Cited

U.S. PATENT DOCUMENTS 3,860,818   1/1975   Stalder et al. .................. 250/343

*Primary Examiner*—Davis L. Willis
*Attorney, Agent, or Firm*—Allen J. Jaffe; David J. Zobkiw

[57] ABSTRACT

A demountable, rectangular, liquid sample flow cell is provided which can be used to make streaming potential or streaming current measurements from which the zeta potential is calculated. By providing an infrared transparent window in the flow cell, a real-time monitoring of surface deposition rates and amounts can be determined by infrared radiometry. Because the flow cell is completely demountable, direct analysis of the internal surfaces exposed to the flowing solution is possible.

8 Claims, 7 Drawing Figures

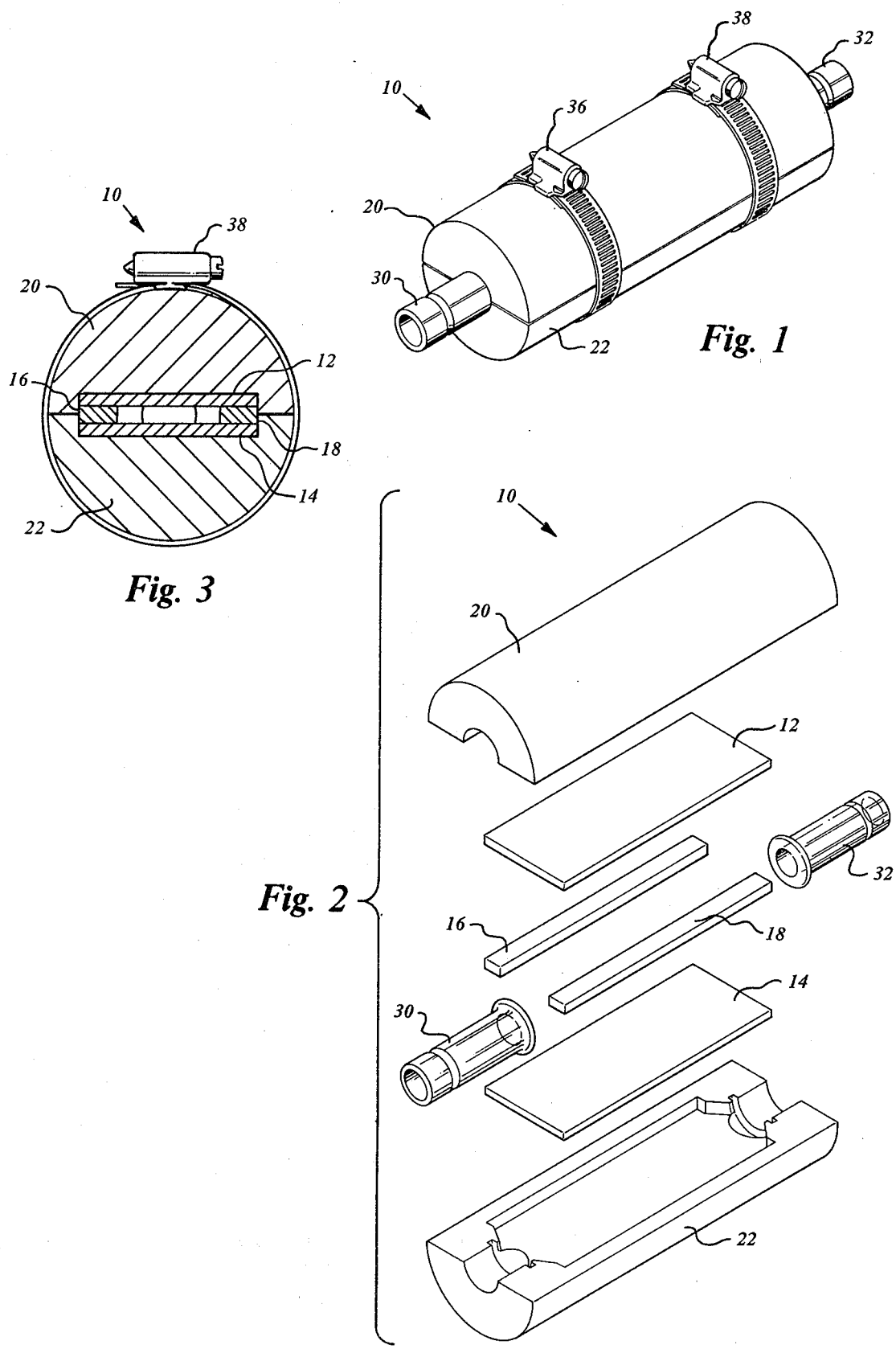

FLOW CELL AND METHOD FOR CONTINUOUSLY MONITORING DEPOSITS ON FLOW SURFACES

There are a number of situations in which a surface is subject to being coated with biological films as from biological fouling in the case of sea water and from adsorption of blood proteins in the case of in vivo implants. The characterization of several surfaces exposed to various blood proteins requires information on the zeta potential of the material making up the surfaces. Basically, two techniqes are available for this determination. First, using the mobility of particles in an electric field, it is possible to make electrophoretic measurements on small (2µdia.) particles from which their zeta potential can be determined. The second technique involves flowing a solution through a circular capillary made of the material of interest. Neither of these techniques lends itself to an examination of the surface nor are they suitable for the complete list of electrical measurements to be made or for a measure of the conformation of the adsorbed protein. If, as in the case of blood proteins, the solution contains adsorbable species, then the adsorbed film thickness, molecular conformation and its wettability could not be obtained using small particles or a capillary of the material.

Microfouling of solid surfaces by spontaneously adsorbed films and then by biological slimes has important efficiency-limiting effects on heat exchangers, and predisposes the surfaces to thicker macrofouling deposits (see Reference). Specific surface properties of the materials (chemical, electrical, textural) strongly influence the nature of the first acquired films, their subsequent resistance to shear-induced detachment and/or cleaning, and their immobilization of boundary liquid layers. The flow cell of the present invention permits a determination at controlled shear rates of the following parameters of the spontaneously adsorbed film: change in streaming (and zeta) potentials; rest potentials; contact potentials; infrared spectra of the initial deposits; film thicknesses and refractive indices; change in critical surface tension; surface texture; and associated inorganic elements prior to mineralization. By providing a window transparent to infrared energy, radiometric measurements of heat transfer parameters in real time as well as values of streaming (and zeta) potentials at a variety of controlled shear rates and shear stresses are possible before, during and after the adsorption of biological films. This arrangement also allows the measurement of normal rest potential for metallic surfaces in equilibrium with their contacting electrolytes and modification of that potential in a "voltage clamping" arrangement in both static and flow experiments. By assembling the flow cell using two internal reflection plates separated by thin glass shims, substituting for the capillary geometry which is normally used for zeta potential measurements, the flow cell can be rapidly taken apart after each flow experiment for the measurement of the infrared absorbing properties, thickness, surface potential and structure of the adsorbed protein films.

It is an object of this invention to provide a method and apparatus for the direct observation of the adsorption process in a protein media.

It is a further object of this invention to provide a demountable flow cell suitable for use in making streaming potential measurements and for the direct analysis of the internal surfaces exposed to the flowing solution.

It is an additional object of this invention to provide a readily disassembled flow cell.

It is a still further object of this invention to provide a method and apparatus for the real-time monitoring of surface deposition rates and amounts by infrared radiometry. These objects, and others as will become apparent hereinafter, are accomplished by the present invention.

Basically, a flow cell is provided which is held assembled in a fluid tight manner by a clamp structure. Where the sample contains an adsorbable species, it will be deposited onto the flow cell surfaces as the solution passes through the cell. By providing surfaces which are optical elements used for internal reflection infrared analysis of the adsorbed species as internal surfaces of the flow cell, measurement of the infrared absorbing properties, thickness, surface potential and structure of the adsorbed protein film can be monitored in real-time and measured upon disassembly of the flow cell.

BRIEF DESCRIPTION OF THE DRAWINGS

For a fuller understanding of the present invention, reference should now be had to the following detailed description thereof taken in conjunction with the accompanying drawings wherein:

FIG. 1 is a perspective view of the flow cell;
FIG. 2 is an exploded view of the flow cell of FIG. 1;
FIG. 3 is a sectional view of the flow cell of FIG. 1.

DESCRIPTION OF THE PREFERRED EMBODIMENTS

Figure 4:
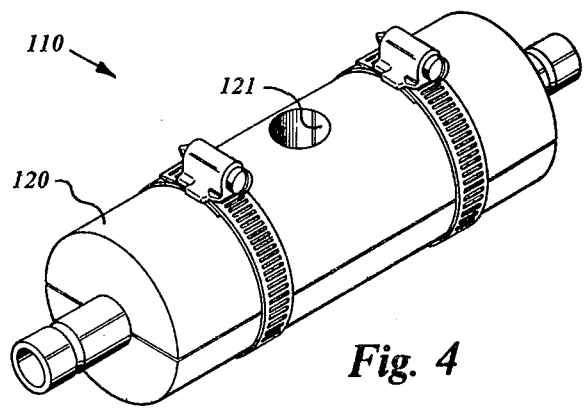
FIG. 4 is a perspective view of a modified flow cell.

Referring to FIGS. 1–3, the numeral 10 generally indicates a flow cell for use in measuring the adsorption of blood proteins. The flow path in the flow cell 10 is defined by germanium or germanium coated plates 12 and 14 which are separated by glass shims 16 and 18. In an actual apparatus used, the n-type germanium plates 12 and 14 were 2×5×0.1 cm thick, the glass shims 16 and 18 were 0.5×5×0.015 cm thick and when assembled formed a 1×0.015 cm flow path through the device, but these dimensions are not critical. The plates 12 and 14 and shims 16 and 18 are held together by housing members 20 and 22 and plates 12 and 14 are received in matching relieved areas in housing members 20 and 22. Flow line members 30 and 32 are received in matching relieved portions of housing members 20 and 22 and form a part of the flow path through the flow cell 10. Housing members 20 and 22 and thereby plates 12 and 14, shims 16 and 18, and flow line members 30 and 32 are held in a proper and fluid tight relationship by hose clamps, or like devices, 36 and 38. The flow cell 10 is readily taken part by removing hose clamps 36 and 38 and this permits the direct measuring of infrared absorbing properties, thickness, surface potential and structure of the adsorbed protein film which forms on the internal surfaces of flow cell 10 at the solid/liquid interface as a protein containing solution flows through the flow cell 10.

Figure 5:
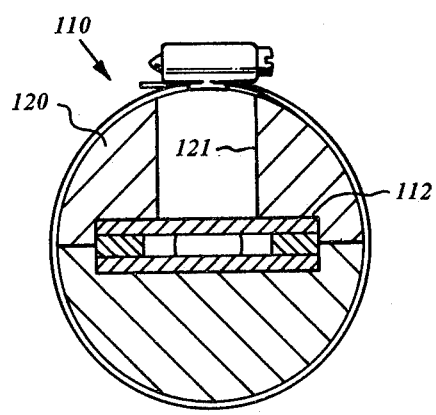
FIG. 5 is a sectional view of the flow cell of FIG. 4.

Because germanium has excellent infrared transmission properties in the sensing range of existing infrared radiometers, the flow cell 10 of FIGS 1–3 may be modified to flow cell 110 of FIGS. 4 and 5 by providing an optical path or window 121 through housing member 120 to germanium or germanium coated plate 112 in housing member 120 to permit real-time monitoring of surface deposition rates and amounts. Flow cell 110 is otherwise identical to flow cell 10 of FIGS. 1–3.

OPERATION

Figure 6:
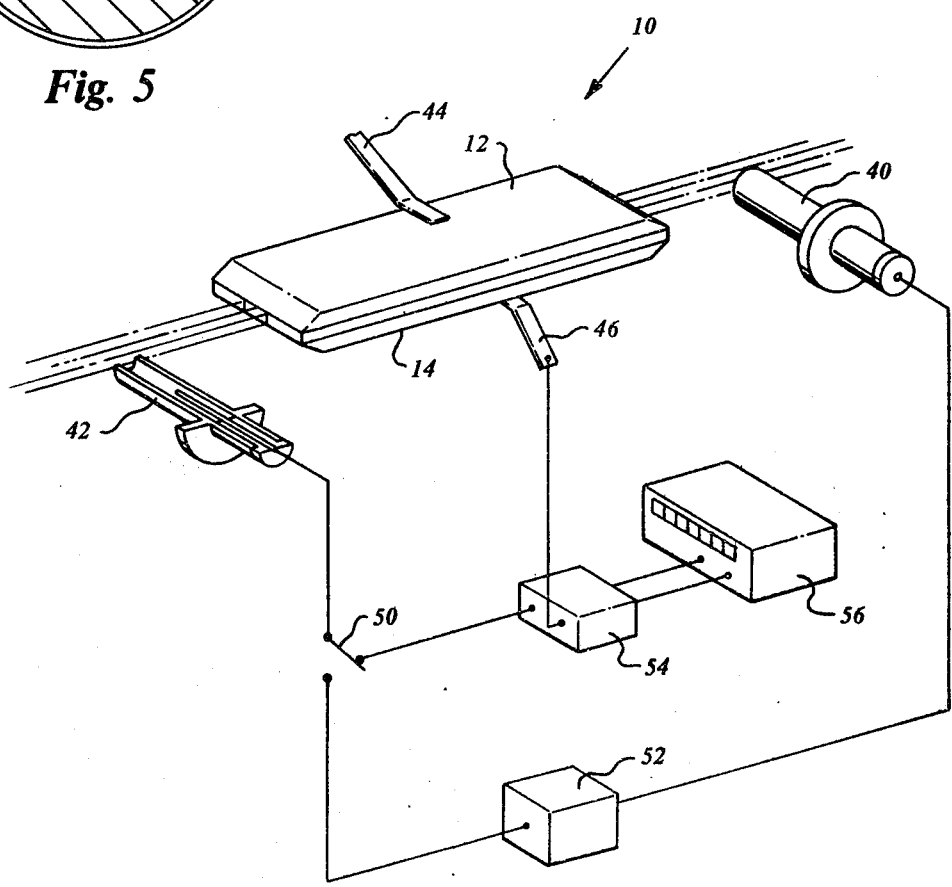
FIG. 6 is a schematic representation of an apparatus employing the flow cell of FIG. 1.

The operation of the flow cell 10 of FIGS. 1–3 is best understood with reference to FIG. 6. The protein-containing electrolyte flows in a fluid path between silver/silver chloride electrodes 40 and 42 via flow cell 10. Platinum ribbons 44 and 46 are provided to make electrical contact with germanium plates 12 and 14, respectively. A number of measurements may be made by varying the electrical connections and providing the proper instrumentation. In the arrangement illustrated, switch 50 is selectively movable to complete an electrical circuit containing electrodes 40 and 42 for measuring streaming potential via differential voltmeter 52. In the other position of switch 50, electrode 42 and plate 14 are connected to digital voltmeter 56 via unity gain high impedance amplifier 54 for measuring the rest potential.

Figure 7:
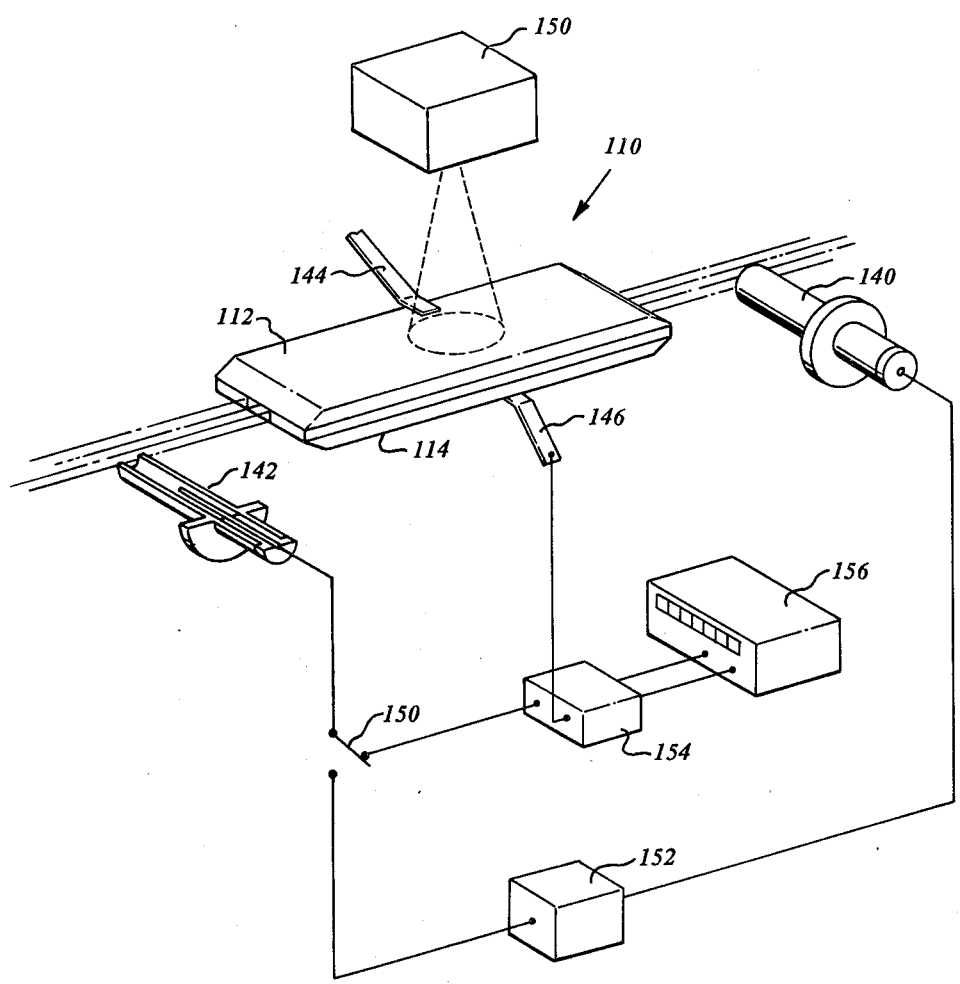
FIG. 7 is a schematic representation of an apparatus employing the modified flow cell of FIG. 4.

The operation of the flow cell 110 of FIG. 4 is best understood with reference to FIG. 7 and is essentially the same as that of the flow cell 10 of FIG. 6. In FIG. 7, structure corresponding to the structure of FIG. 6 is numbered one hundred higher. Flow cell 110 is capable of permitting a real-time monitoring of the conditions within the flow cell through the use of infrared radiometer 150. Because germanium is infrared transparent in plates of relatively thin thicknesses, plate 112 is transparent to the infrared radiation detectable by infrared radiometer 150, and the interior of cell 110 is visible and available for real-time monitoring of surface deposition rates and amounts.

Although preferred embodiments of the present invention have been illustrated and described, other changes will occur to those skilled in the art. For example, the flow cell members have been secured in a fluid tight relationship by end blocks including structure for receiving the electrodes. It is therefore intended that the scope of the present invention is to be limited only by the scope of the appended claims.

REFERENCE

V. A. DePalma and R. E. Baier, "Microfouling of Metallic and Coated Metallic Flow Surfaces in Model Heat Exchange Cells", a paper presented and passed out at the OTEC Conference in Seattle, October, 1977.

We claim:

1. A demountable flow cell having an inlet and an outlet with a flow path therebetween and including:
   a pair of mating housing members having corresponding recesses located therein;
   first and second plates receivable in respective ones of said corresponding recesses;
   shim means for separating said first and second plates when the flow cell is assembled and to define with said plates a portion of said flow path;
   means for holding said housing members in an assembled, flight tight relationship while permitting disassembly of said flow cell to permit direct examination of said plates defining said flow path.

2. The flow cell of claim 1 wherein one of said housing members has an optical path extending from the recess therein through said one housing member.

3. The flow cell of claim 2 wherein said first and second plates are transparent to infrared radiation.

4. A demountable flow cell for the direct examination of the adsorption process in a protein media including:
   first means defining a first flow path surface;
   second means defining a second flow path surface;
   third means for separating said first and second means; and
   fourth means for demountably securing said first, second and third means in a fluid tight relationship while permitting disassembly of said flow cell to permit direct examination of said first and second means.

5. The flow cell of claim 4 wherein at least one of said first and second means is transparent to infrared radiation.

6. A method for directly examining deposits on flow surfaces including the steps of:
   flowing a sample containing an adsorbed species through a flow cell;
   disassembling the flow cell; and
   directly examining the internal surfaces of the flow cell.

7. A method for continuously monitoring deposits on flow surfaces including the steps of:
   flowing a sample containing an adsorbed species through a flow cell having a portion which is infrared transparent;
   monitoring deposits on the flow cell surfaces through the use of an infrared radiometer.

8. The method of claim 7 further including the steps of:
   disassembling the flow cell; and,
   directly examining the internal surfaces of the flow cell.

* * * * *

UNITED STATES PATENT OFFICE
CERTIFICATE OF CORRECTION

PATENT NO. : 4,175,233
DATED : November 20, 1979
INVENTOR(S) : V. A. DePalma et al.

It is certified that error appears in the above-identified patent and that said Letters Patent are hereby corrected as shown below:

Column 4, line 12, change "flight" to -- fluid --.

Signed and Sealed this

Twenty-ninth Day of April 1980

[SEAL]

Attest:

Attesting Officer

SIDNEY A. DIAMOND

Commissioner of Patents and Trademarks